(12) United States Patent
Nishino et al.

(10) Patent No.: US 10,682,372 B2
(45) Date of Patent: Jun. 16, 2020

(54) INTRACELLULAR ATP ENHANCER

(71) Applicant: StaGen Co., Ltd., Tokyo (JP)

(72) Inventors: Takeshi Nishino, Tokyo (JP); Naoyuki Kamatani, Tokyo (JP)

(73) Assignee: STAGEN CO., LTD., Tokyo (JP)

(*) Notice: Subject to any disclaimer, the term of this patent is extended or adjusted under 35 U.S.C. 154(b) by 0 days.

(21) Appl. No.: 15/754,842

(22) PCT Filed: Aug. 24, 2016

(86) PCT No.: PCT/JP2016/074644
§ 371 (c)(1),
(2) Date: Feb. 23, 2018

(87) PCT Pub. No.: WO2017/033963
PCT Pub. Date: Mar. 2, 2017

(65) Prior Publication Data
US 2018/0243326 A1 Aug. 30, 2018

(30) Foreign Application Priority Data
Aug. 26, 2015 (JP) .................... 2015-166372

(51) Int. Cl.
A61K 31/426 (2006.01)
A61K 31/708 (2006.01)
A61K 31/4439 (2006.01)
A61K 31/405 (2006.01)
A61K 9/20 (2006.01)
A61K 31/415 (2006.01)
A61K 45/06 (2006.01)
A61K 31/522 (2006.01)
A61K 31/045 (2006.01)
A61K 31/519 (2006.01)

(52) U.S. Cl.
CPC .......... A61K 31/708 (2013.01); A61K 9/2054 (2013.01); A61K 9/2059 (2013.01); A61K 31/045 (2013.01); A61K 31/405 (2013.01); A61K 31/415 (2013.01); A61K 31/426 (2013.01); A61K 31/4439 (2013.01); A61K 31/519 (2013.01); A61K 31/522 (2013.01); A61K 45/06 (2013.01)

(58) Field of Classification Search
CPC .. A61K 31/708; A61K 31/426; A61K 9/2054; A61K 45/06
USPC .......................................................... 514/45
See application file for complete search history.

(56) References Cited

U.S. PATENT DOCUMENTS 8,318,792 B2 11/2012 Nishino et al.
8,916,713 B2 12/2014 Chatterjee et al.
2005/0277614 A1 12/2005 Benowitz

FOREIGN PATENT DOCUMENTS

PL 2598494 T3 3/2015
RU 2212241 C2 9/2003

OTHER PUBLICATIONS

Nomura et al. Xanthine Oxidase Inhibition by Febuxostat Attenuates Experimental Atherosclerosis in Mice. Sci. Rep. 4, 4554; p. 1-9. DOI:10.1038/srep04554 (Apr. 1, 2014). (Year: 2014).*
Spitsin et al. Inactivation of peroxynitrite in multiple sclerosis patients after oral administration of inosine may suggest possible approaches to therapy of the disease. Multiple Sclerosis (2001) 7, 313-319. (Year: 2001).*
Crowell et al. Effect of allopurinol on hemorrhagic shock. American Journal of Physiology 216(4):744-748, 1969. (Year: 1969).*
Lee et al. Effect of Acute Xanthine Oxidase Inhibition on Myocardial Energetics During Basal and Very High Cardiac Workstates. J. of Cardiovasc. Trans. Res. (2011) 4:504-513. (Year: 2011).*
Kurashiro et al., "Xanthine oxidase inhibitor," Heart View (2013), vol. 17, No. 2, pp. 184-186, ISSN 1342-6591, p. 185, middle column, paragraph of '(2) Febuxostat with English translation.
Borkowski et al., "Protection of Mouse Heart Against Hypoxic Damage by AMP Deaminase Inhibition," Nucleosides, Nucteotides and Nucleic Acids (2010), Vol. 29, pp. 449-452.
De Jong et al., "Hereditary Spherocytosis and Elliptocytosis Erythrocytes Show a Normal Transbilayer Phospholipid Distribution," Blood (Jul. 1, 1999), Vol. 94, No. 1, pp. 319-325.
English translation of International Search Report dated Oct. 4, 2016, in PCT International Application No. PCT/JP2016/074644.
Gallardo et al., "An α2-Na/K ATPase/α-adducin complex in astrocytes triggers non-cell autonomous neurodegeneration," Nat. Neurosci. (Dec. 2014), vol. 17, No. 12, pp. 1710-1719.
Glader, B. E., "Salicylate-Induced Injury of Pyruvate-Kinase-Deficient Erythrocytes," N. Engl. J. Med. (Apr. 22, 1976), vol. 294, No. 17, pp. 916-918.
Harmsen et al., "Enhanced ATP and GTP synthesis from hypoxanthine or inosine after myocardial ischemia," Am. J. Physiol. (1984), vol. 246, No. 1 Pt. 2, pp. H37-H43.
Houghton et al., "Combinations of 5-FU, Hypoxanthine, and Allopurinol in Chemotherapy for Human Colon Adenocarcinoma Xenografts," Cancer Treat. Rep. (1982), vol. 66, pp. 1201-1206.

(Continued)

Primary Examiner — Yih-Horng Shiao
(74) Attorney, Agent, or Firm — Birch, Stewart, Kolasch & Birch, LLP

(57) ABSTRACT

A problem to be solved by the present invention is to provide a substance having an effect of increasing intracellular ATP and, particularly, a potent ATP enhancer far surpassing the increasing effect of inosine or febuxostat alone.

A human or animal intracellular ATP enhancer comprising a combination of A) and B):

A) a xanthine oxidase/xanthine dehydrogenase inhibitor or a pharmaceutically acceptable salt thereof; and B) any one or more compounds selected from inosine, inosinic acid, hypoxanthine, and pharmaceutically acceptable salts thereof.

7 Claims, 10 Drawing Sheets

(56) References Cited

OTHER PUBLICATIONS

Ichida, K, Febuxostat (TMX-67), Puricase (PEG-uricase), Nippon Rinshio (2008), vol. 66, No. 4, pp. 759-765.

Kurashiro et al., "Xanthine Sanka Koso Sogaiyaku," Heart View (2013), vol. 17, No. 2, pp. 184-186.

Loh et al., "Common Variant in AMPD1 Gene Predicts Improved Clinical Outcome in Patients with Heart Failure," Circulation (1999), vol. 99, pp. 1422-1425.

Markowitz et al., "The Treatment of Multiple Sclerosis with Inosine." The Journal of Alternative and Complementary Medicine (2009), vol. 15, No. 6, pp. 619-625.

McNaughton et al., "Inosine Supplementation Has No Effect on Aerobic or Anaerobic Cycling Performance," Int. J. Sport Nutr. (Dec. 1999), vol. 9, No. 4, pp. 333-344.

Mentzer et al., "Hereditary Stomatocytosis: Membrane and Metabolism Studies," Blood (Nov. 1975), vol. 46, No. 5, pp. 659-669.

Noman et al., "Effect of high-dose allopurinol on exercise in patients with chronic stable angina: a randomised, placebo controlled crossover trial," The Lancet (Jun. 19, 2010), vol. 375. pp. 2161-2167.

Norman et al., "Regulation of skeletal muscle ATP catabolism by AMPD1 genotype during sprint exercise in asymptomatic subjects," J. Appl. Physiol. (2001), vol. 91, pp. 258-264.

Notification of Reasons for Refusal dated Apr. 5, 2017, in Japanese Patent Application No. 2016-572842, with English translation.

Ogasawara et al., "Deficiency of AMP deaminase in erythrocytes," Hum. Genet. (1987), vol. 75, pp. 15-18.

Palek et al., "Crosslinking of the nearest membrane protein neighbors in ATP depleted, calcium enriched and irreversibly sickled red cells," Prog. Clin. Biol. (1978), vol. 20, pp. 75-91.

Schwarzschild et al., The Parkinson Study Group, SURE-PD Investigators, "Inosine to increase serum and CSF urate in Parkinson disease: A randomised, placebo-controlled trial," JAMA Neurol. (Feb. 1, 2014), vol. 71, No. 2, pp. 141-150.

Settle et al., "Effect of Allopurinol and Inosine Administration on Xanthine Oxidoreductase Gene Expression in Selected Tissues of Broiler Chickens," International Journal of Poutry Science (2015), vol. 14, No. 1, pp. 37-43.

Vogt et al., "Lactate accumulation rather than ATP depletion predicts ischemic myocardial necrosis. Implications for the development of lethal myocardial injury," Biochimica et Biophysica Acta (2001), vol. 1586, pp. 219-226.

Wang et al., "Allopurinol preserves myocardial energy metabolism in chronic heart failure rats," Journal of Clinical Cardiology (China) (2015) vol. 31, No. 1, pp. 89-93.

Wiley et al., "Increased Erythrocyte Cation Permeability in Thalassemia and Conditions of Marrow Stress," J. Clin. Invest. (Apr. 1981), vol. 67, pp. 917-922.

Extended European Search Report dated Mar. 15, 2019, in European Patent Application No. 16839310.6.

Kamatani et al., "Treatment of two mitochondrial disease patients with a combination of febuxostat and inosine that enhances cellular ATP," Journal of Human Genetics (2019), vol. 64, pp. 351-353.

Yamamoto et al, "Effect of TEI-6720, a Xanthine Oxidase Inhibitor, on the Nucleoside Transport in the Lung Cancer Cell Line A549," Pharmacology (2000), vol. 60, pp. 34-40.

English translation of International Preliminary Report on Patentability and Written Opinion dated Mar. 8, 2018, in PCT International Application No. PCT/JP2016/074644.

Chinese Office Action and Search Report, dated Dec. 4, 2019, for Chinese Application No. 201680049519.6.

Hirsch et al., "Allopurinol Acutely Increases Adenosine Trlphospate Energy Delivery . . . " Heart Failure, Journal of the American Colleage of Cardiology, vol. 59, No. 9, Feb. 28, 2012, pp. 802-808.

Jurkowitz et al., "Adenosine, Inosine, and Guanosine Protect Glial Cells During Glucose Deprivation and Mitochondrial Inhibition: Correlation Between Protection and ATP Preservation," Journal of Neurochemistry, vol. 71, No. 2, 1998, pp. 535-548.

Russian Office Action and Search Report for Russian Application No. 2018110363, dated Jan. 28, 2020, with English translation.

* cited by examiner

[Fig.1]
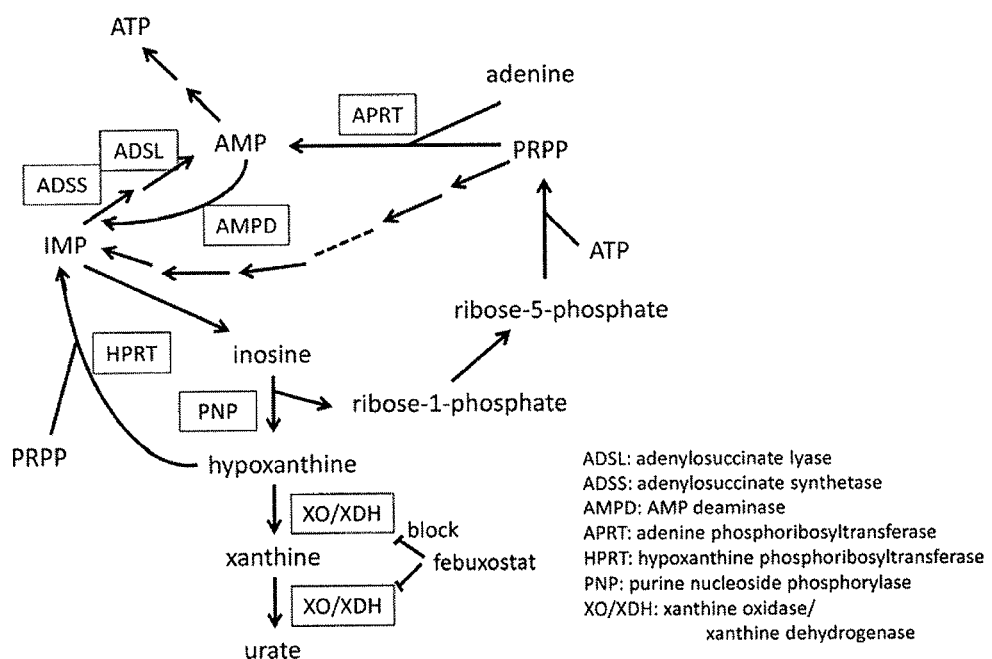

[Fig.2]
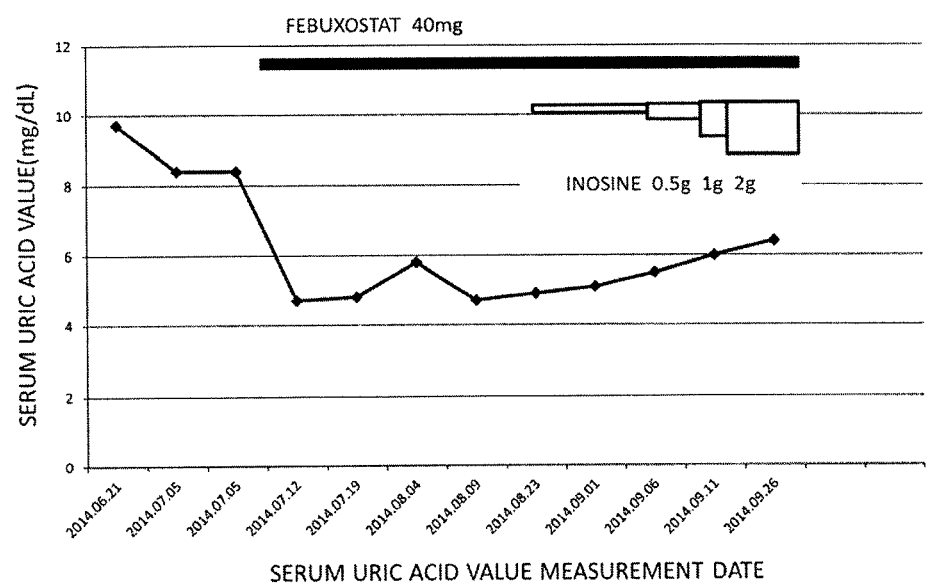

[Fig.3]
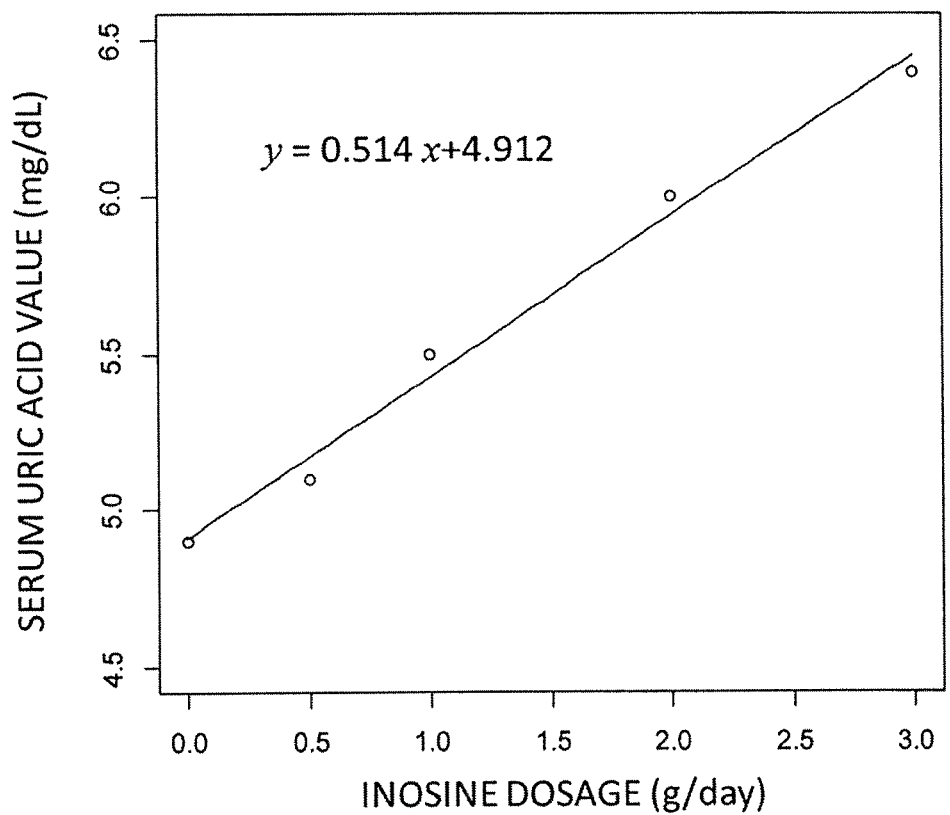

[Fig.4]
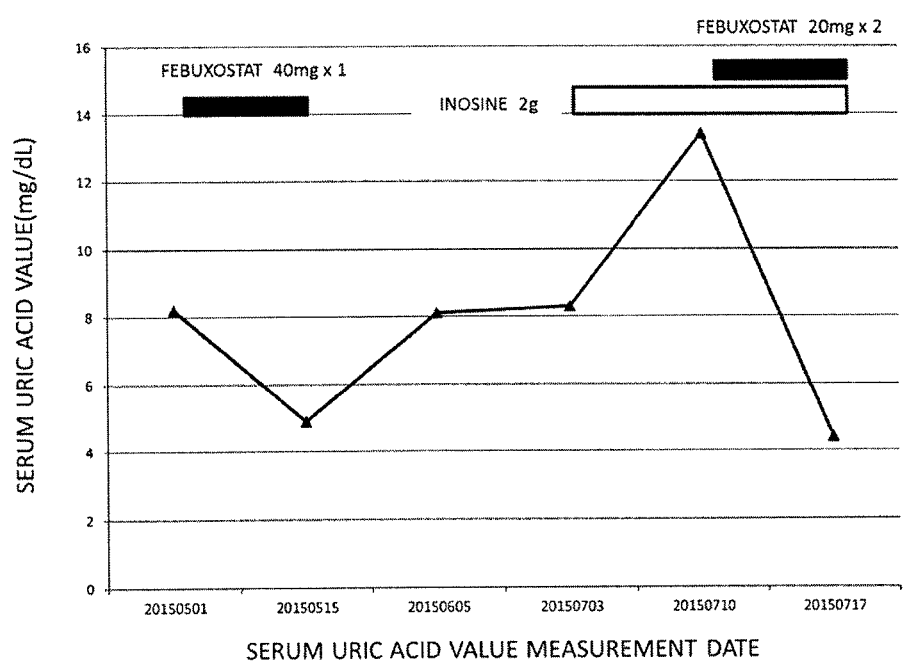

[Fig.5]

AMOUNT OF PURINES IN BLOOD (ALL IN μmol/L)

| | FEBUXOSTAT (40 mg) + INOSINE (2 g) | none | MULTIPLYING FACTOR |
|---|---|---|---|
| ATP | 134 | 128 | 1.05 |
| IMP | 0.731 | 0.629 | 1.16 |
| URIC ACID | 43.9 | 81.6 | 0.54 |
| HYPOXANTHINE | 5.04 | 0.185 | 27.32 |
| XANTHINE | 5.69 | 0.988 | 5.76 |
| INOSINE | 0.0816 | 0.0494 | 1.65 |

[Fig.6]
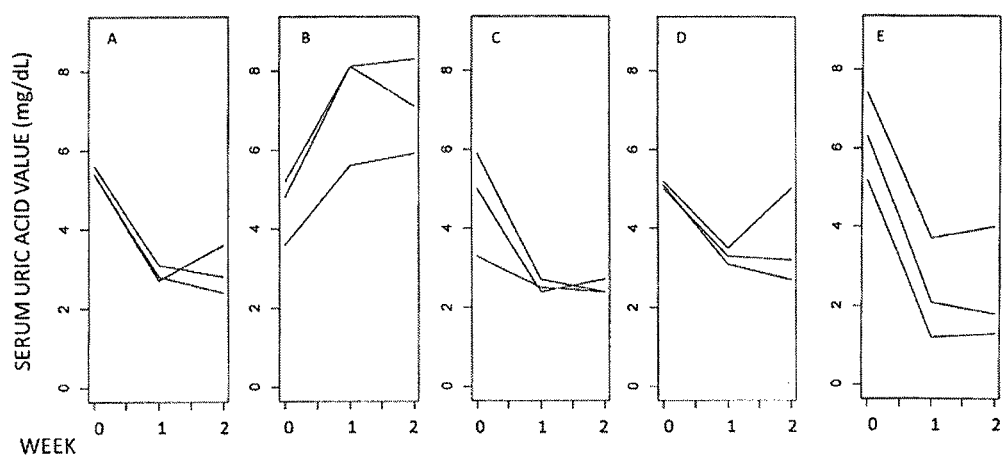

[Fig.7]
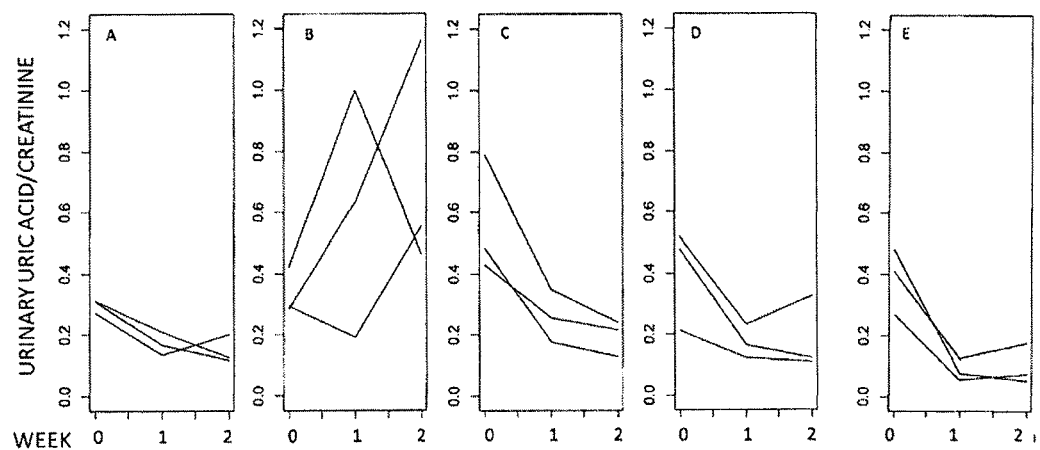

[Fig.8]
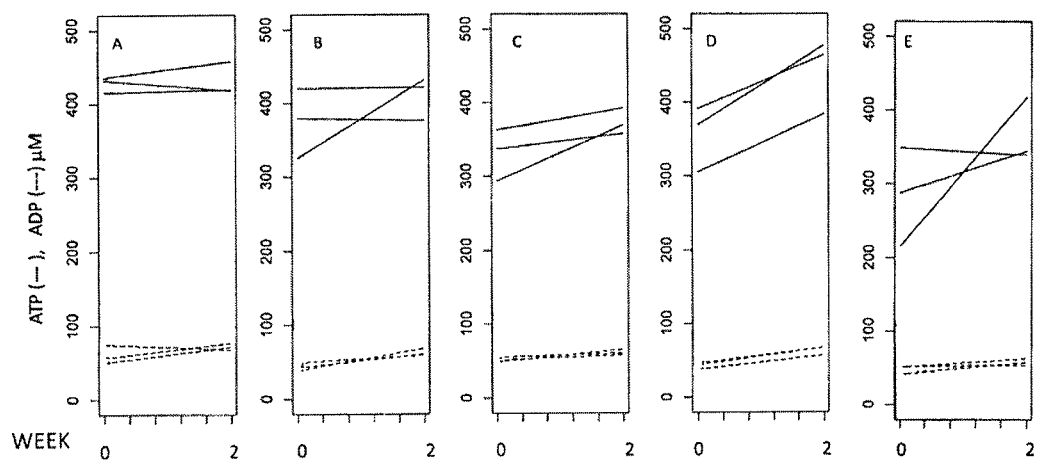

[Fig.9]
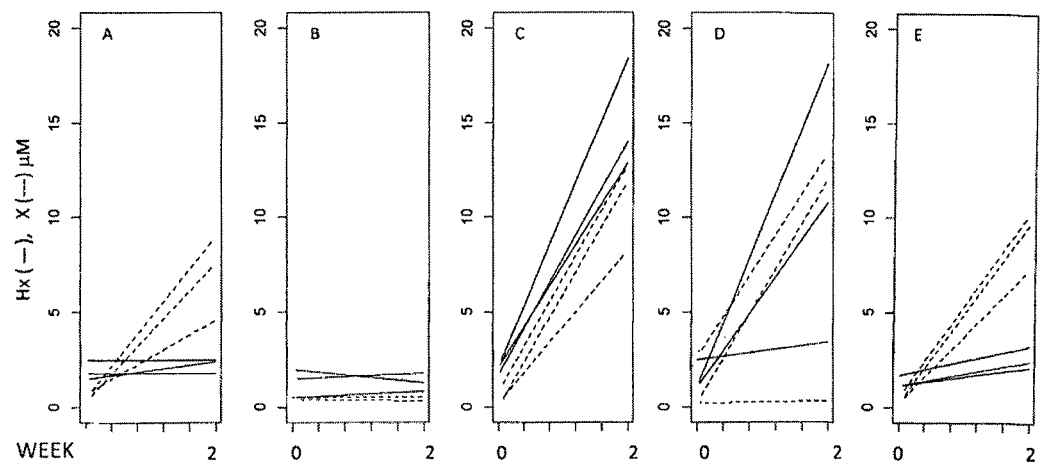

[Fig.10]

| SUBJECT ID | 2 | 3 | 4 | 5 | 6 | 7 | 8 | 9 | 10 |
|---|---|---|---|---|---|---|---|---|---|
| | GROUP A | | | GROUP B | | | GROUP C | | |
| DAY 1 | | | | | | | | | |
| Ino (µM) | 0.6 | 7.2 | 18.3 | 3 | 27.5 | 20.3 | 3.1 | 1.2 | 0.4 |
| HX (µM) | 6.4 | 25.2 | 131.6 | 11.3 | 114.5 | 74.8 | 31.2 | 7.2 | 2.8 |
| X (µM) | 6.4 | 17.6 | 142.4 | 5.7 | 121.9 | 36.9 | 12.9 | 3.7 | 3.1 |
| UA (µM) | 103.1 | 647 | 2133.7 | 281.5 | 1881.7 | 1975.5 | 831.2 | 216.5 | 168.8 |
| DAY 15 | | | | | | | | | |
| Ino (µM) | 0.9 | 0.9 | 1.3 | 2.4 | 13 | 1.4 | 10.5 | 13.4 | 9.4 |
| HX (µM) | 78.6 | 86.5 | 206.8 | 11.2 | 47.7 | 72.9 | 690.3 | 1331.5 | 2256.7 |
| X (µM) | 320.7 | 541.5 | 556 | 11.7 | 61.9 | 33.7 | 493.1 | 2023.3 | 1190.4 |
| UA (µM) | 210.5 | 726.9 | 728.7 | 1021.2 | 1544.6 | 511.3 | 293.4 | 1239.1 | 1045.6 |

| SUBJECT ID | 11 | 12 | 13 | 14 | 15 | 16 |
|---|---|---|---|---|---|---|
| | GROUP D | | | GROUP E | | |
| DAY 1 | | | | | | |
| Ino (µM) | 24.9 | 2.4 | 4.2 | 0.8 | 29.2 | 7.5 |
| HX (µM) | 62.7 | 50 | 7.1 | 3.2 | 47.4 | 117.2 |
| X (µM) | 33 | 25.9 | 4.2 | 6.7 | 50.3 | 80.6 |
| UA (µM) | 1617 | 1526.3 | 518 | 282.3 | 2639 | 2198.5 |
| DAY 15 | | | | | | |
| Ino (µM) | 29.1 | 3.1 | 17.4 | 0.6 | 0.8 | 6 |
| HX (µM) | 1965.1 | 131.8 | 949.9 | 11.2 | 77.2 | 314 |
| X (µM) | 1474.8 | 22.7 | 1063.6 | 81.7 | 273.1 | 867.7 |
| UA (µM) | 649.2 | 1610.7 | 658.7 | 22.8 | 398.9 | 289.3 |

INTRACELLULAR ATP ENHANCER

TECHNICAL FIELD

The present invention relates to a human or animal intracellular ATP enhancer. More specifically, the present invention relates to a human or animal intracellular ATP enhancer comprising a combination of A) a xanthine oxidase/xanthine dehydrogenase inhibitor or a pharmaceutically acceptable salt thereof and B) any one or more compounds selected from inosine, inosinic acid, hypoxanthine, and pharmaceutically acceptable salts thereof.

BACKGROUND ART

ATP (adenosine triphosphate, hereinafter sometimes simply referred to as ATP) is the most important compound that stores energy of living organisms and supplies the energy when necessary, and it is considered that ATP reduction is related to pathological conditions of various diseases. For example, with regard to the causes of various types of hereditary hemolytic anemia, ATP reduction in erythrocytes is considered as a mechanism of hemolysis. Examples include sickle cell disease (Non-Patent Document 1), pyruvate kinase deficiency (Non-Patent Document 2), spherocytosis (Non-Patent Document 3), elliptocytosis (Non-Patent Document 3), stomatocytosis (Non-Patent Document 4), thalassemia (Non-Patent Document 5), etc.

Additionally, intracellular ATP reduction is suggested as a mechanism of myocardial damage due to ischemic heart disease (Non-Patent Document 6), and it is reported that symptoms of chronic stable angina were suppressed by high-dose administration of a xanthine oxidase/xanthine dehydrogenase inhibitor, allopurinol (Non-Patent Document 7). The authors suggested that an increase in ATP due to allopurinol had a favorable effect on ischemic heart disease (Non-Patent Document 7).

Furthermore, an ATP enhancement therapy is likely to be effective for heart failure. Heart failure patients often undergo heart transplantation in US and, instead of a period from occurrence of heart failure to death, a period from occurrence of heart failure to heart transplantation is used as a measure of a speed of progress of heart failure. A short period until heart transplantation indicates that the progress of heart failure is fast. In Europe and US, the frequency of hereditary muscle AMP deaminase (AMPD) deficiency is extremely high, and about 20% of the general population has heterozygous deficiency. It is known from studies that people with muscle genetic AMPD deficiency have a longer period from heart failure to heart transplantation (Non-Patent Document 8). It is also suggested that an AMPD inhibitor improves heart failure in mice (Non-Patent Document 9). Generally, ATP of muscle decreases due to exercise. However, it is reported that people with hereditary muscle AMPD deficiency have intramuscular ATP not decreasing, or restrained from decreasing, after exercise (Non-Patent Document 10). Specifically, since AMP is not converted into IMP (inosine monophosphate, hereinafter sometimes simply referred to as IMP), AMP reduction can be prevented and ATP reduction does not occur (FIG. 1). From above, it is considered that genetic muscle AMPD deficiency was less likely to cause ATP reduction in cardiomyocytes and suppressed the progress of heart failure.

It can be expected that enhancing ATP in this way improves pathological conditions of diseases in which a decrease in ATP relates to the pathological conditions.

Although it is reported that inosine enhances muscular movement in expectation of occurrence of an enhancing action on muscular movement due to ATP increased by administration of inosine, a report denying the effect thereof is also made recently (Non-Patent Document 11). However, it is possible that a cause of inability to prove inosine's muscular enhancing action is because inosine alone is not sufficient for completing the ATP enhancing action.

Nishino et al. have found that a xanthine oxidase/xanthine dehydrogenase inhibitor such as febuxostat administered to a model mouse of amyotrophic lateral sclerosis (hereinafter sometimes simply referred to as ALS) inhibits disease progression (Non-Patent Document 12). Allopurinol did not inhibit the disease progression. Nishino et al. speculate that an increase in ATP of nerve cells due to administration of febuxostat suppresses disease progression (Non-Patent Document 12). Nishino et al. speculate that a reason that allopurinol does not have an effect is because allopurinol consumes PRPP and inhibits ATP synthesis to the contrary (Non-Patent Document 12). In fact, it is reported that knock-down of Na/K-ATPase in ALS model mice suppressed degeneration of nerve cells (Non-Patent Document 12). It is also reported that Na/K-ATPase activity is increased in ALS patients (Non-Patent Document 13). Therefore, it is considered that activation of Na/K-ATPase that reduces ATP promotes the onset or progression of ALS and that suppression of Na/K-ATPase that suppresses ATP reduction suppresses the progress of ALS.

Furthermore, it is reported that administration of inosine alleviates symptoms of Parkinson's disease (Non-Patent Document 14) and multiple sclerosis (Non-Patent Document 15). The authors of both documents believe that a decrease in serum uric acid value may be related to the diseases. Clinical trials are conducted for the purpose of raising the serum uric acid value by administering inosine, and producing a therapeutic effect. However, the effect is not enough in the past reports.

It has been reported that intracellular ATP somewhat increases due to single administration of inosine. In fact, Ogasawara et al. reported that ATP increased when erythrocytes allowed to stand at low temperature for 20 to 30 days and reduced in ATP were allowed to stand for one hour after addition of inosine (Non-Patent Document 16). However, inosine is rapidly metabolized in human bodies through hypoxanthine and xanthine to uric acid (FIG. 1). Therefore, inosine alone was insufficient to produce the sufficient ATP enhancing action. Additionally, although single administration of febuxostat is expected to somewhat enhance intracellular ATP, this alone may be insufficient.

FREE TEXT CITATION LIST

Non Patent Literature

Non-Patent Document 1: Palek J, Liu S C, Liu P A. Crosslinking of the nearest membrane protein neighbors in ATP depleted, calcium enriched and irreversibly sickled red cells. Prog Clin Biol Res. 1978; 20:75-91.

Non-Patent Document 2: Glader B E. Salicylate-induced injury of pyruvate-kinase-deficient erythrocytes. N Engl J Med. 1976 Apr. 22; 294(17):916-8.

Non-Patent Document 3: de Jong K, Larkin S K, Eber S, Franck P F, Roelofsen B, Kuypers F A. Hereditary spherocytosis and elliptocytosis erythrocytes show a normal transbilayer phospholipid distribution. Blood. 1999 Jul. 1; 94(1):319-25.

Non-Patent Document 4: Mentzer W C Jr, Smith W B, Goldstone J, Shohet S B. Hereditary stomatocytosis: membrane and metabolism studies. Blood. 1975 November; 46(5):659-69.

Non-Patent Document 5: Wiley J S. Increased erythrocyte cation permeability in thalassemia and conditions of marrow stress. J Clin Invest. 1981 April; 67(4):917-22.

Non-Patent Document 6: Vogt A M, Ackermann C, Yildiz M, Schoels W, Kubler W. Lactate accumulation rather than ATP depletion predicts ischemic myocardial necrosis: implications for the development of lethal myocardial injury. Biochim Biophys Acta. 2002 Mar. 16; 1586(2): 219-26

Non-Patent Document 7: Noman A, Ang D S, Ogston S, Lang C C, Struthers A D. Effect of high-dose allopurinol on exercise in patients with chronic stable angina: a randomised, placebo controlled crossover trial. Lancet. 2010 Jun. 19; 375(9732):2161-7.

Non-Patent Document 8: Loh E, Rebbeck T R, Mahoney P D, DeNofrio D, Swain J L, Holmes E W. Common variant in AMPD1 gene predicts improved clinical outcome in patients with heart failure. Circulation. 1999 Mar. 23; 99(11):1422-5.

Non-Patent Document 9: Borkowski T, Slominska E M, Orlewska C, Chlopicki S, Siondalski P, Yacoub M H, Smolenski R T. Protection of mouse heart against hypoxic damage by AMP deaminase inhibition. Nucleosides Nucleotides Nucleic Acids. 2010 June; 29(4-6):449-52.

Non-Patent Document 10: Norman B, Sabina R L, Jansson E. Regulation of skeletal muscle ATP catabolism by AMPD1 genotype during sprint exercise in asymptomatic subjects. J Appl Physiol (1985). 2001 July; 91(1):258-64.

Non-Patent Document 11: McNaughton L, Dalton B, Tarr J. Inosine supplementation has no effect on aerobic or anaerobic cycling performance. Int J Sport Nutr. 1999 December; 9(4):333-44.

Non-Patent Document 12: Yasuko Abe, Shinsuke Kato, Takeshi Nishino. Therapeutic agent for amyotrophic lateral sclerosis. U.S. Pat. No. 8,318,792 B2, European Patent EP2050467 A1

Non-Patent Document 13: Gallardo G, Barowski J, Ravits J, Siddique T, Lingrel J B, Robertson J, Steen H, Bonni A. An α2-Na/K ATPase/α-adducin complex in astrocytes triggers non-cell autonomous neurodegeneration. Nat Neurosci. 2014 December; 17(12): 1710-9.

Non-Patent Document 14: Parkinson Study Group SURE-PD Investigators, Schwarzschild M A, Ascherio A, Beal M F, Cudkowicz M E, Curhan G C, Hare J M, Hooper D C, Kieburtz K D, Macklin E A, Oakes D, Rudolph A, Shoulson I, Tennis M K, Espay A J, Gartner M, Hung A, Bwala G, Lenehan R, Encamacion E, Ainslie M, Castillo R, Togasaki D, Barles G, Friedman J H, Niles L, Carter J H, Murray M, Goetz C G, Jaglin J, Ahmed A, Russell D S, Cotto C, Goudreau J L, Russell D, Parashos S A, Ede P, Saint-Hilaire M H, Thomas C A, James R, Stacy M A, Johnson J, Gauger L, Antonelle de Marcaida J, Thurlow S, Isaacson S H, Carvajal L, Rao J, Cook M, Hope-Porche C, McClurg L, Grasso D L, Logan R, Orme C, Ross T, Brocht A F, Constantinescu R, Sharma S, Venuto C, Weber J, Eaton K. Inosine to increase serum and cerebrospinal fluid urate in Parkinson disease: a randomized clinical trial. JAMA Neurol. 2014 February; 71(2):141-50.

Non-Patent Document 15: Markowitz C E, Spitsin S, Zimmerman V, Jacobs D, Udupa J K, Hooper D C, Koprowski H. The treatment of multiple sclerosis with inosine. J Altern Complement Med. 2009 June; 15(6):619-25.

Non-Patent Document 16: Ogasawara N, Goto H, Yamada Y, Nishigaki I, Itoh T, Hasegawa I, Park K S. Deficiency of AMP deaminase in erythrocytes. Hum Genet. 1987 January; 75(1):15-8.

SUMMARY OF INVENTION

Technical Problem

A problem to be solved by the present invention is to provide a composition having an effect of enhancing intracellular ATP, and, particularly, an ATP enhancer surpassing the enhancing effect of inosine or febuxostat alone.

Furthermore, it is desired to provide a new ATP enhancer and an ATP enhancing method that suppresses an increase in serum uric acid value due to inosine when inosine is administered to enhance ATP Solution to Problem To solve the problems described above, the present invention has the following configurations.

<1> A human or animal intracellular ATP enhancer comprising a combination of A) and B):

A) a xanthine oxidase/xanthine dehydrogenase inhibitor or a pharmaceutically acceptable salt thereof; and B) any one or more compounds selected from inosine, inosinic acid, hypoxanthine, and pharmaceutically acceptable salts thereof.

<2> The intracellular ATP enhancer according to <1>, wherein the xanthine oxidase/xanthine dehydrogenase inhibitor is any one or more selected from febuxostat, topiroxostat (FUJIYAKUHIN), allopurinol, hydroxyalkane, carprofen, and Y-700 (Mitsubishi Tanabe Pharma).

<3> The ATP enhancer according to <1> or <2>, wherein the ATP enhancer is in the form of a combination drug or a kit formulation.

<4> Febuxostat used in combination with inosine as an intracellular ATP enhancer.

<5> A pharmaceutical product that is a combination drug or a kit formulation comprising a combination of A) and B):

A) a xanthine oxidase/xanthine dehydrogenase inhibitor or a pharmaceutically acceptable salt thereof; and B) any one or more compounds selected from inosine, inosinic acid, hypoxanthine, and pharmaceutically acceptable salts thereof.

The present invention also provides the following administration methods.

<6> A method of enhancing intracellular ATP in human or animal, comprising the step of administering to a human or an animal A) and B):

A) a xanthine oxidase/xanthine dehydrogenase inhibitor or a pharmaceutically acceptable salt thereof; and B) any one or more compounds selected from inosine, inosinic acid, hypoxanthine, and pharmaceutically acceptable salts thereof.

<7> The method of enhancing intracellular ATP according to <6>, wherein the xanthine oxidase/xanthine dehydrogenase inhibitor is any one or more selected from febuxostat, topiroxostat (FUJIYAKUHIN), allopurinol, hydroxyalkane, carprofen, and Y-700 (Mitsubishi Tanabe Pharma).

<8> The method of enhancing intracellular ATP according to <6> or <7>, wherein A) and B) are a combination drug including A) and B).

<9> A method of enhancing intracellular ATP comprising the step of administering A) and B) to a patient with hemolytic anemia, ischemic heart disease, heart failure, amyotrophic lateral sclerosis, Parkinson's disease, or ADSL deficiency:

A) a xanthine oxidase/xanthine dehydrogenase inhibitor or a pharmaceutically acceptable salt thereof; and B) any one or more compounds selected from inosine, inosinic acid, hypoxanthine, and pharmaceutically acceptable salts thereof.

Advantageous Effects of Invention

The ATP enhancing effect of the combined administration of A) and B) of the present invention enables provision of a drug for treating various diseases in which the reduction of ATP forms a portion of pathological conditions, furthermore various diseases in which progression of the pathological conditions is suppressed by excessive supply of ATP:

A) a xanthine oxidase/xanthine dehydrogenase inhibitor or a pharmaceutically acceptable salt thereof; and B) any one or more compounds selected from inosine, inosinic acid, hypoxanthine, and pharmaceutically acceptable salts thereof.

BRIEF DESCRIPTION OF DRAWINGS

FIG. 1 is a diagram of a route related to ATP synthesis.

FIG. 2 is a graph of a schedule of combined administration of febuxostat and inosine, and transition of serum uric acid value. The horizontal axis indicates a serum uric acid value measurement date and the vertical axis indicates the serum uric acid value (in mg/dL).

FIG. 3 is a graph of a result of regression analysis analyzing a relationship between an inosine dosage and a serum uric acid value. The horizontal axis indicates a daily dosage (in g/day) of inosine, the vertical axis indicates the serum uric acid value (in mg/dL), and the equation in the figure is the equation expressing a regression line. In this equation, x is the daily dosage of inosine and y is the serum uric acid value.

FIG. 4 is a graph of a schedule of single administration of febuxostat or inosine and combined use of both drugs, and transition of serum uric acid value. The horizontal axis indicates a serum uric acid value measurement date (e.g., 20150501 represents May 1, 2015), and the vertical axis indicates the serum uric acid value (in mg/dL).

FIG. 5 is a diagram comparing amounts of various purines in peripheral blood when febuxostat and inosine are used in combination and when no drug is taken. The amounts of purines are all expressed as a molar amount within 1 L of whole blood. Febuxostat (40 mg)+inosine (2 g): Values when febuxostat and inosine are used in combination. None: Values when no drug is taken.

FIG. 6 is a graph of transition of serum uric acid values in the case of administration to Groups A to E. The horizontal axis indicates a measurement period (week), and the vertical axis indicates the serum uric acid value (in mg/dL). Group A: Febuxostat 20 mg twice a day for 14 days, Group B: inosine 500 mg twice a day for 14 days, Group C: Febuxostat 20 mg+inosine 500 mg twice a day for 14 days, Group D: Febuxostat 20 mg+inosine 1000 mg twice a day for 14 days, Group E: febuxostat 30 mg twice a day for 14 days (the same applies to the following figures).

FIG. 7 is a graph of transition of urinary uric acid concentration/creatinine concentration in the case of administration to Groups A to E. The horizontal axis indicates a measurement period (week), and the vertical axis indicates the urinary uric acid concentration/creatinine concentration (ratio).

FIG. 8 is a graph of comparison of ATP and ADP in blood in the case of administration to Groups A to E. The horizontal axis indicates a measurement period (week), and the vertical axis indicates the ATP or ADP concentration (in M). ATP: Solid line, ADP: Broken line.

FIG. 9 is a graph of comparison of Hx (hypoxanthine) and X (xanthine) in blood in the case of administration to Groups A to E. The horizontal axis indicates a measurement period (week), and the vertical axis indicates the Hx or X concentration (in µM). Hx: Solid line, X: Dashed line.

FIG. 10 is a diagram comparing concentrations (µM) of various purines in urine in the case of administration to Groups A to E.

DESCRIPTION OF EMBODIMENTS

One active ingredient of the present invention is A) a xanthine oxidase/xanthine dehydrogenase inhibitor or a pharmaceutically acceptable salt thereof. Examples of the xanthine oxidase/xanthine dehydrogenase inhibitor include febuxostat, topiroxostat (FUJIYAKUHIN), allopurinol, hydroxyalkane, carprofen, and Y-700 (Mitsubishi Tanabe Pharma), among which febuxostat is desirable.

Another active ingredient of the present invention is B) any one or more compounds selected from inosine, inosinic acid, hypoxanthine, and pharmaceutically acceptable salts thereof. Among them, inosine is desirable.

The intracellular ATP enhancer of the present invention refers to an effect that the active ingredients of the present invention increase generation of ATP in the cells. The increase is used to mean either increasing, or suppressing of decrease, from a steady state, or bringing a reduced state closer to the steady state. The effect of the present invention can be confirmed by directly measuring the intracellular ATP concentration as well as by indirectly measuring a product of another metabolic pathway induced by an increase in ATP.

"Comprising a combination of A) and B)" of the present invention is used to mean all the forms in which the components A) and B) are combined such that the components are administered to exert an ATP enhancing action in the body of a subject of administration. Therefore, this includes either a combination drug of the components A) and B) mixed to form a composition, or drugs presented together to be administered in the same period at the time of administration although physically present separately without being mixed. Examples of the combination drug of the components A) and B) mixed to form a composition include those mixed as a drug formulation. Examples of drug formulation include oral agents such as granules, powders, solid formulations, and liquids. Examples of the drugs presented together to be administered in the same period at the time of administration although physically present separately include a so-called kit formulation and a form of being packed in one bag. The same period does not necessarily mean the same time in a strict sense, and the same period of the present invention includes the case that an interval exists within a range in which the ATP enhancing effect of the present invention is exerted. For example, when one is taken before meal and the other is taken after meal, this corresponds to the case of administering in the same period of the present invention.

The dosage of the present invention is desirably 10 to 80 mg/day per day for febuxostat of A). The dosage is desirably 0.5 to 4.0 g/day for inosine of B).

With regard to an administration method, each of the dosages can be administered once a day, or divided twice or more a day. Among them, febuxostat is desirably administered twice a day rather than once a day as in a conventional usage of febuxostat. It is also desirable that inosine is administered twice a day rather than once a day. Therefore, both inosine and febuxostat are more desirably divided and administered twice a day.

In the case of a combination drug, adjustment may be made in consideration of a daily dosage and an administration method, and febuxostat and inosine may desirably be adjusted by adding 0.5 g, 1 g, 1.5 g, or 2 g of inosine to 20 mg or 40 mg of febuxostat.

The subject of administration of the present invention is a human or an animal and is a human or an animal in a condition requiring enhancement of ATP.

Target diseases include the following diseases in which a relation of ATP reduction to pathological conditions is strongly suggested, i.e., (1) hemolytic anemia, (2) ischemic heart disease, (3) heart failure, (4) amyotrophic lateral sclerosis, (5) Parkinson's disease, and (6) ADSL deficiency. Among them, the present invention is particularly effective for (2) ischemic heart disease, (3) heart failure, and (4) amyotrophic lateral sclerosis.

The ATP enhancer of the present invention can further be combined with other medicines within the range not to impair the action of the present invention.

The present invention will now specifically be described based on examples; however, the present invention is not limited thereto.

EXAMPLES

[Test Example 1] First Administration Test
(Combined Administration)

1. Measurement Method of Serum Uric Acid Value

For a clinical chemistry automatic analyzer, a dry clinical chemistry analysis measuring unit manufactured by ARKRAY, Inc. was used, and the serum uric acid value was measured by using the uricase-peroxidase method.

2. Administration Test
(1) Subject of Administration
Human, age 67, male, height 180 cm, weight 77 kg
(2) Administration Schedule The administration schedule is shown in FIG. 2. A first clinical test was conducted by first administering febuxostat at 40 mg/day (single administration of febuxostat), after a while, additionally administering inosine (combined administration of febuxostat and inosine), and gradually increasing the dosage of inosine from 0.5 to 3 g/day. Meanwhile, blood was collected at the timing shown on the horizontal axis of FIG. 2 to measure the serum uric acid value.

3. Serum Uric Acid Value Measurement Result

The serum uric acid value of each of the administration periods is shown in FIG. 2. According to this result, the uric acid value decreased from 8.4 mg/dL (2014.07.05) to 4.7 mg/dL (2014.07.12) as expected due to administration of febuxostat at 40 mg/day. Subsequently, as a result of administering inosine in a gradually increasing manner from 0.5 g/day to 3 g/day in addition to febuxostat, the serum uric acid values at the time of administration of 0 g, 0.5 g, 1 g, 2 g, and 3 g of inosine were 4.9 (2014.08.23), 5.1 (2014.9.01), 5.5 (2014.09.06), 6.0 (2014.09.11), and 6.4 (2014.09.26) mg/dL, respectively, and regression analysis revealed that the serum uric acid value increased at the rate of 0.51 mg/dL per 1 g of inosine (FIG. 3). This can be seen from the regression line in FIG. 3 having the slope of 0.51. Therefore, it is considered that when x (inosine) increases by 1, y (serum uric acid value) increases by 0.51. Even the administration of 40 mg/day of febuxostat and 3 g/day of inosine caused no adverse event at all.

[Test Example 2] Second Administration Test

1. Measurement Method of Serum Uric Acid Value
Same as Test Example 1.
2. Administration Test
(1) The subject of administration was the same as Test Example 1.
(2) Administration Schedule The administration schedule is shown in FIG. 4. After a sufficient period had elapsed from completion of Test Example 1, febuxostat was administered again at 40 mg/day to the patient, and the serum uric acid value was measured three days later. Subsequently, febuxostat was discontinued and, after a while, administration of 2 g/day of inosine was started (administered at 1 g each after breakfast and dinner) and was followed by combined use of 2 g/day of inosine and 40 mg of febuxostat (administered at 20 mg each after breakfast and dinner). The serum uric acid value was measured at time points shown on the horizontal axis of FIG. 4.

3. Serum Uric Acid Value Measurement Result

The serum uric acid value of each of the administration periods is shown in FIG. 4. The serum uric acid value measured after three days from the administration of 40 mg/day of febuxostat was reduced by 3.4 mg/dL from 8.2 mg/dL (20150501) before the administration to 4.8 mg/dL (20150515) after the administration. This is almost the same as the reduction of 3.7 mg/dL in the previous test.

Subsequently, febuxostat was discontinued, and it was confirmed that the serum uric acid value returned to 8.1 mg/dL (20150605) and 8.3 mg/dL (20150703), which were almost the same as the previous value (FIG. 4). Administration of 2 g/day of inosine (administration of 1 g each after breakfast and dinner) was started from 20150704 and the serum uric acid value measured six days later was extremely raised to 13.4 mg/dL. Specifically, since the value was raised by 5.1 mg/dL due to the administration of 2 g/day of inosine, the value was raised by 2.55 mg/dL per 1 g/day administration of inosine. Subsequently, as a result of combined use with 40 mg of febuxostat (administered at 20 mg each after breakfast and dinner), the serum uric acid value was 4.4 mg/dL (20150717) (FIG. 4). An adverse event did not occur at all.

[Test Example 3] Third Administration Test

1. Analysis Method
(1) Measurement Method of Purines

Various purines in peripheral blood were measured according to Reference (1). Briefly, peripheral blood was collected with EDTA, mixed with 500 μL+500 μL ice cold 8% PCA, immediately vortexed for five seconds, and centrifuged at 12,000×g for 10 minutes at 4° C., and the supernatant was stored at −80° C. The sample was dissolve in a gathered state, and 40 μL of 2M $K_2CO_3$ in 6 M KOH was added to 650 μL of the solution to precipitate PCA and neutralize the solution at the same time. After this solution was centrifuged at 12,000×g for 10 minutes at 4° C., 160 μL of a mobile phase was added to 40 μL of supernatant and apply to HPLC. The conditions of HPLC were also set according to Reference (1) below. The amounts of purines are expressed in molar quantity contained in 1 L of whole blood.

Reference (1): Coolen E J, Arts I C, Swennen E L, Bast A, Stuart M A, Dagnelie P C. Simultaneous determination of adenosine triphosphate and its metabolites in human whole blood by RP-HPLC and UV-detection. J Chromatogr B Analyt Technol Biomed Life Sci. 2008 Mar. 15; 864(1-2): 43-51.

(2) Measurement Method of Uric Acid

Same as Test Example 1.

2. Administration Test (1) The subject of administration was the same as Test Example 1.

(2) Administration Schedule

The combined use of 2 g/day of inosine (administered at 1 g each after breakfast and dinner) and 40 mg of febuxostat (administered at 20 mg each after breakfast and dinner), blood was collected seven days later for measurement of various purines in peripheral blood (febuxostat (40 mg)+ inosine 2 g of FIG. 5). Subsequently, all the drugs were discontinued, and blood was collected seven days later for measurement of various purines in the peripheral blood (none of FIG. 5).

3. Test Results

The test results are shown in FIG. 5. Although the uric acid value at the time of combined use of inosine and febuxostat was 0.54 times higher than that when no drug was taken, this is a reasonable value because the result of the second administration test, the serum uric acid value without taking drug was 8.2, 8.1, and 8.3 mg/dL, while the serum uric acid value was 4.4 mg/dL at the time of 2 g/day of inosine (administered at 1 g each after breakfast and dinner) and 40 mg of febuxostat (administered at 20 g each after breakfast and dinner), therefore, 4.4/8.1=0.54 is obtained. Thus, the serum uric acid value at the time of combined use of 2 g/day of inosine and 40 mg/day of febuxostat is about ½ of that when no drug is administered.

Although ATP was increased 1.05 times due to drug administration, this is reasonable since the administration experiment was conducted to a normal person with no decrease in ATP recognized. A normal person has sufficient ATP and needs no further enhancement. IMP is extremely small in amount as compared to ATP (IMP amount is 1/204 of ATP amount in the absence of drug) and is increased 1.16 times due to drug administration (FIG. 5). Thus, the combined use of inosine and febuxostat results in a slight increase in IMP. The most significantly increased purine is hypoxanthine as expected. Hypoxanthine was increased 27.3 times (FIG. 5). Inosine and xanthine were increased 1.65 times and 5.76 times, respectively. Although the administration of inosine at 2 g per day, inosine was only slightly increased, which indicates that inosine was consumed for increasing hypoxanthine. Fortunately, an increasement of xanthine which associated with a report of calculi is limited. Obviously, an increase in uric acid is significantly suppressed due to febuxostat.

This experiment was conducted for a normal person, and a normal person has sufficient ATP and needs no further enhancement. No significant increase was generated due to the combined use of inosine and febuxostat. However, since hypoxanthine was significantly increased, it is considered that when ATP is insufficient, the circuit for replenishing ATP immediately works (FIG. 1).

Furthermore, the combined use of inosine and febuxostat resulted in only slight increases in inosine and xanthine and even caused a decrease in uric acid. Only hypoxanthine was significantly increased. The increase in xanthine was also relatively small and is an amount causing no problem as compared to the amount of uric acid. This indicates that the combined use of inosine and febuxostat has a low possibility of crystalluria and calculi.

4. Discussion about the First to Third Test Results

Comparing the results of the second test with the results of the first test, since the serum uric acid value was raised by 0.51 mg/dL per 1 g/day of inosine administered in the presence of 40 mg/day of febuxostat in the first test, febuxostat suppressed the increase in serum uric acid value due to inosine to 0.51/2.55=1/4.47.

Therefore, it was found that although febuxostat has the actions of lowering and inosine has the actions of increasing, respectively, the serum uric acid value, the serum uric acid increasing action of inosine is considerably suppressed (to 1/4.47, or 22.4%) by febuxostat. In other words, febuxostat not only lowers the serum uric acid value but also considerably suppresses the serum uric acid increasing action of inosine.

The data that febuxostat largely suppressed the serum uric acid increasing action of inosine suggests that, because of the action of febuxostat, hypoxanthine acquired from inosine is largely increased due to the suppression of xanthine oxidase/xanthine dehydrogenase. This was confirmed by the result of the third test (FIG. 5). This increase is considered to be much larger than single administration of inosine. This is because it is considered that, as can be seen in the increase in serum uric acid value, the administration of inosine alone has an insufficient hypoxanthine increasing action due to being immediately metabolized to uric acid and is also insufficient in terms of ATP enhancement. In fact, in the third test, the combined use of inosine and febuxostat resulted in a slight increase in inosine. A large portion was consumed to increase hypoxanthine. It is considered that this hypoxanthine contributes to ATP enhancement.

Probably, this is because purine nucleoside phosphorylase (PNP) acts on inosine, resulting in immediate conversion to hypoxanthine and ribose-1-phosphate (FIG. 1). It is considered that both hypoxanthine and ribose-1-phosphate generated in this way play a role of enhancing ATP (FIG. 1). Moreover, it is considered that since febuxostat strongly suppresses xanthine oxidase/xanthine dehydrogenase, the decomposition of hypoxanthine to xanthine is suppressed and the concentration of hypoxanthine is increased, which further acts as a supply source of purine compounds. This is supported by the fact that only the increase in hypoxanthine was very large at the time of combined use of febuxostat and inosine (FIG. 5). Hypoxanthine reacts with PRPP due to the HPRT enzyme and synthesize IMP (FIG. 1). Through two reactions, IMP turns into AMP, which turns into ATP On the other hand, it is considered that ribose-1-phosphate acts as a supply source of PRPP through ribose-5-phosphate and that PRPP binds to adenine due to the action of adenine phosphoribosyltransferase (APRT) to generate AMP, thereby further increasing AMP concentration. It is also thought that the actions of PRPP increasing the de novo purine synthesis and serving as a substrate of HPRT to increase the IMP also play a significant role.

The important thing is the administration method of febuxostat when inosine and febuxostat are used in combination. When 40 mg/day of febuxostat and 2 g/day of inosine were administered, inosine was administered at 1 g each after breakfast and dinner in both the first and second tests. However, febuxostat was administered once at 40 mg after breakfast in the first test and was administered twice at 20 mg each after breakfast and dinner in the second test. The serum uric acid value was 6.0 mg/dL in the former and 4.4 mg/dL in the latter, resulting in a large difference of 1.5 mg/dL. This is thought to be because administering 20 mg twice a day has a stronger effect of lowering the serum uric acid value than administering 40 mg of febuxostat once a day. Therefore, when febuxostat is used in combination with inosine, it is desirable to administer febuxostat twice a day as inosine, rather than once a day as in the conventional usage of febuxostat.

[Test Example 4] Clinical Test (Combined Administration)

Although the administered subject was the same in the first to third administration tests, in the present test, the test subjects were expanded to confirm that the first to the third test results are correct.
1. Various Measurement Methods
(1) Clinical Examination
Measurement was performed by conventional methods except the following items.
(2) Serum Uric Acid Value
Same as Test Example 1.
(3) Urinary Uric Acid Concentration/Creatinine Concentration
Since the urinary uric acid concentration varies with urine volume, a urinary uric acid amount was evaluated by using a urinary uric acid/creatinine value acquired by dividing by urinary creatinine concentration. The measurement method of the uric acid value was the same as Test Example 1.
(4) Blood Purine Concentration
Same as Test Example 3.
(5) Urinary Purine Concentration
Same as Test Example 3.
2. Administration Test
(1) Test Subjects
The following administration test was conducted for 16 Japanese healthy adult males, one subject in Phase I and 15 subjects which divided into Groups of A to E for each groups 3 subjects in phase II.
(2) Administration Schedule
(2-1) Phase I
Safety was confirmed by simultaneous administration of 20 mg of febuxostat and 500 mg of inosine twice a day for 14 days to one subject.
(2) Phase II
After the end of Phase I, administration was performed to three subjects of each of the groups as follows:
Group A: febuxostat 20 mg twice a day for 14 days;
Group B: inosine 500 mg twice a day for 14 days;
Group C: febuxostat 20 mg+inosine 500 mg twice a day for 14 days;
Group D: febuxostat 20 mg+inosine 1000 mg twice a day for 14 days; and
Group E: febuxostat 30 mg twice a day for 14 days.
3. Results
3-1. Phase I
(1) Adverse Events
(1-1) Physical Findings Etc.
The subjects had no adverse events in terms of subjective findings and physical findings.
(1-2) Clinical Examination
AST showed an abnormal value of 49 U/L (reference value: 10 to 40) on Day 8 and returned to a reference value of 29 U/L on Day 15. The creatinine showed an abnormal value of 1.09 mg/dL (reference value: 0.61 to 1.04) on Day 8 and returned to a reference value of 0.98 mg/dL on Day 15.

The blood glucose level showed an abnormal value of 66 mg/dL on Day 8 and 67 mg/dL on Day 15 (reference value: 70 to 109).
(2) Change in Uric Acid Value
The serum uric acid value was 4.9 mg/dL on Day 1, 2.5 mg/dL on Day 8, and 2.9 mg/dL on Day 15. Taking 40 mg of febuxostat and 1 g of inosine resulted in a reduction of 2.2 mg/dL on average.
3-2. Phase II
(1) Adverse Events
(1-1) Physical Findings
No significant difference existed between groups in terms of age, height, weight, BMI, systolic blood pressure, diastolic blood pressure, pulse rate, and body temperature. No significant change was seen in systolic blood pressure, diastolic blood pressure, pulse rate, and body temperature, except a significant increase in the pulse rate observed in one subject.
(1-2) Adverse Events of Test Values (Excluding Uric Acid Value)
Measurement was performed on total protein, albumin, total bilirubin, AST, ALT, AL-P, LD, γ-GT, total cholesterol, neutral fat, HDL cholesterol, LDL cholesterol determinate quantity, uric acid, urea nitrogen, creatinine, sodium, chloride, potassium, calcium, blood glucose test, HbA1c (NGSP), white blood cell count WBC, red blood cell count RBC, hemoglobin level Hb, hematocrit Ht, platelet count PLT, BASO, EOSINO, NEUTRO, LYMPH, and MONO.
No particular difference was observed in the background of the groups. No particular significant change was recognized except the serum uric acid value.
(2) Change in Serum Uric Acid Value
FIG. 6 shows graphs of respective Groups A to E. A significant increase in serum uric acid value was observed in Group B to which only inosine was administered (up to 8.1 mg/dL). In Groups A, C to E, a decrease in serum uric acid value was observed. The serum uric acid value was not reduced to less than 2 mg/dL in any of the administration examples of 40 mg/day of febuxostat; however, the serum uric acid value less than 2 mg/dL was observed in the example of Group E to which 60 mg/day of febuxostat was administered.
The serum uric acid value was reduced by 2.53 mg/dL due to the administration of 40 mg/dL of febuxostat (Group A), and was reduced by 2.23 mg/dL (Group C) and 1.47 mg/dL (Group D) in the examples of administering 1 g or 2 g per day of inosine, respectively, at the same time of febuxostat administration.
The serum uric acid value was reduced by 3.93 mg/dL due to administration of 60 mg/dL of febuxostat (Group E). The serum uric acid value was raised by 2.57 mg/dL on average due to 1 g per day of inosine (Group B). Examining this result in terms of the serum uric acid value increasing effect of inosine in the presence of administration of febuxostat, the serum uric acid value was increased by 0.3 mg/dL due to 1 g/day administration of inosine, and was increased by 1.06 mg/dL due to 2 g/day administration of inosine, in the presence of 40 mg/day of febuxostat. As described above, the serum uric acid value was increased by 2.57 mg/dL due to 1 g/day administration of inosine without administration of febuxostat, and therefore, the serum uric acid raising action of inosine is considerably suppressed in the presence of administration of febuxostat.
(3) Urinary Uric Acid Concentration/Creatinine Concentration
Changes in urinary uric acid concentration/creatinine concentration of the respective groups from Week 0 to Week 2 are shown in FIG. 7. The urinary uric acid/creatinine was significantly increased only in Group B due to administration of inosine. The urinary uric acid/creatinine was reduced in all of Groups A and C to G. These changes in the urinary uric acid concentration/creatinine concentration were almost the same as the change pattern of the serum uric acid value.

(4) Blood Purine Concentration

Changes in concentrations of purines in blood of the respective groups from Week 0 to Week 2 are shown in FIG. 8 to 9.

FIG. 8 shows the concentration of blood ATP/ADP in Groups A to E. The ATP concentration was not changed in Groups A and B, and a rise in ATP was suggested in Groups C and D. No certain tendency was observed in Group E. Therefore, although no rise in ATP was observed due to single administration of febuxostat or inosine, a rise in ATP was observed in the combined use examples, especially in the examples of 40 mg/day of febuxostat and 1 to 2 g/day of inosine. No certain tendency was observed from the combined use of febuxostat and inosine exceeding these amounts.

FIG. 9 shows the concentrations of hypoxanthine (Hx) and xanthine (X) in blood for each of Groups A to E. In the group of administration of 40 mg/day of febuxostat alone (Group A), the Hx concentration was unchanged, while X was significantly increased. In the group of administration of 1 g/day of inosine alone (Group B), neither Hx nor X changed. Although the inosine concentration in blood was also measured, no rise in the concentration of inosine was observed in any groups including the groups of single administration of inosine (Groups A to E). From these results, it is considered that the concentration of the enzyme converting inosine to Hx, i.e., purine nucleoside phosphorylase (PNP), is extremely high in blood, resulting in a rapid decomposition of inosine to Hx and further decomposition of Hx to X. In the examples of using 40 mg/day of febuxostat in combination with 1 to 2 g/day of inosine, a significant rise was recognized in both Hx and X. Therefore, the effect of "rise in Hx in blood" not observed with febuxostat alone or inosine alone was observed due to the combined use (FIG. 9).

In the single administration example of 60 mg/day of febuxostat, a slight rise in Hx was observed along with a rise in X (FIG. 9E).

(5) Urinary Purine Concentration

Changes in concentrations of urinary inosine, Hx, X, and uric acid of the respective groups from Week 0 to Week 2 are shown in FIG. 10. The urinary Hx showed a moderate rise in the single administration example of febuxostat and showed a significant rise in the combined use example of febuxostat and inosine. In the single administration example of inosine, no rise in Hx or X was recognized. Although the concentration of X significantly increased also in the single administration example of febuxostat, the concentration was further significantly increased in the combined use example of febuxostat and inosine.

The maximum concentrations of urinary X in the respective groups were 556.0 μM in Group A, 61.9 μM in Group B, 2023.3 μM in Group C, 1474.8 μM in Group D, and 867.7 μM in Group E. Therefore, in the examples of using 40 mg of febuxostat in combination with 1 and 2 g of inosine, the maximum urinary X concentrations were 3.64 and 2.65 times larger as compared to the single administration group of 40 mg of febuxostat.

4. Discussion for Test Example 4

(1) The combined use of febuxostat and inosine was safe at a dosage equal to or less than 40 mg/day of febuxostat and 2 g/day of inosine in the two-week continuous dosing test. Although an increase in ATP in blood was observed in these combined use groups, such a change was not observed in the other single administration groups.

(2) A significant decrease in the serum uric acid value were observed in the single administration of febuxostat, a significant increase in the serum uric acid value were observed in the single administration of inosine, and a moderate reduction was observed in the combined therapy.

(3) No increase in inosine was observed in any group and it was considered that inosine was metabolized to Hx by PNP.

(4) In the single administered group of inosine, Hx or X did not increase in blood or urine, and it was considered that Hx and X were changed to uric acid.

(5) In the single administration group of febuxostat, X moderately increased and Hx increased to a slight to moderate degree in both blood and urine.

(6) In the combined use of febuxostat and inosine, Hx and X significantly increased in both blood and urine. It is considered that an increase in Hx in blood causes an increase in ATP.

(7) From the clinical test described above, a pharmacological action, which was impossible for single administration of inosine or febuxostat, was recognized from the combined use thereof. The present invention enables the enhancement of hypoxanthine and ATP in blood, which is a novel pharmacological action that has not existed before.

[Formulation Example] Example of Combination Drug

A combination drug (tablet type) for oral administration was manufactured, having the following contents per tablet.
Febuxostat: 20 mg
Inosine: 0.5 g
Alpha starch (disintegrating binder): 70 mg
Silicifited microcrystalline cellulose (filler): 32.656 mg
Croscarmellose sodium (disintegrant): 10 mg
Magnesium stearate (lubricant): 0.8 mg

[Formulation Example] Example of Kit Formulation

Tablets having the composition of A below containing febuxostat and a medicine having the composition of B below containing inosine were manufactured and put in the same bag separated to prevent mixing with each other for adjustment into one dose. A kit formulation was manufactured by packing two doses, i.e., a daily dosage, thereof in the same box.
A. Febuxostat tablets
Febuxostat: 20 mg
Alpha starch (disintegrating binder): 70 mg
Silicifited microcrystalline cellulose (filler): 32.656 mg
Croscarmellose sodium (disintegrant): 10 mg
Magnesium stearate (lubricant): 0.8 mg
B. Inosine
Inosine: 0.5 g

INDUSTRIAL APPLICABILITY

Intracellular ATP was able to be enhanced by combined administration of febuxostat and inosine. This is a new pharmacological action different from conventional drugs.

Therefore, the present invention is considered to be effective for various diseases having ATP reduction as a pathological condition.

Additionally, the uric acid value raising action of inosine was suppressed by the combined use with febuxostat. Therefore, for patients to which febuxostat is administered for treatment of hyperuricemia, ATP can be increased without decreasing the therapeutic effect on hyperuricemia.

The invention claimed is:

1. A method of enhancing intracellular ATP in human or animal, comprising the step of:
   administering orally to a human or an animal in need thereof an effective amount of A) and B):
   A) febuxostat or a pharmaceutically acceptable salt thereof; and
   B) one or more compounds selected from the group consisting of inosine, inosinic acid, hypoxanthine, and pharmaceutically acceptable salts thereof.

2. The method of enhancing intracellular ATP according to claim 1, wherein A) and B) are combined as a drug composition comprising A) and B).

3. A method of enhancing intracellular ATP, the method comprising the step of administering orally an effective amount of A) and B) to a patient in need thereof, wherein the patient has hemolytic anemia, ischemic heart disease, heart failure, amyotrophic lateral sclerosis, Parkinson's disease, or adenylosuccinate lyase (ADSL) deficiency:
   A) febuxostat or a pharmaceutically acceptable salt thereof; and
   B) one or more compounds selected from the group consisting of inosine, inosinic acid, and pharmaceutically acceptable salts thereof.

4. The method of claim 1, wherein B) is inosine or a pharmaceutically acceptable salt thereof.

5. The method of claim 3, wherein B) is inosine or a pharmaceutically acceptable salt thereof.

6. The method of claim 1 for enhancing intracellular ATP in human.

7. The method of claim 3, wherein the patient is a human patient.

* * * * *